United States Patent [19]

Meyer

[11] Patent Number: 4,666,627
[45] Date of Patent: May 19, 1987

[54] 4-HETEROCYCLYLVINYL-4-'STYRYL-BIPHENYLS

[75] Inventor: Hans R. Meyer, Binningen, Switzerland

[73] Assignee: Ciba-Geigy Corporation, Ardsley, N.Y.

[21] Appl. No.: 635,099

[22] Filed: Jul. 27, 1984

[30] Foreign Application Priority Data

May 8, 1983 [CH] Switzerland .................... 4266/83

[51] Int. Cl.[4] .................... C09K 11/06; C07D 251/12; C07D 261/08
[52] U.S. Cl. .......................... 252/301.22; 252/301.23; 252/301.24; 544/208; 544/211; 544/217; 544/218; 544/219; 544/180; 544/311; 544/313; 544/314; 544/317; 544/318; 544/319; 544/321; 544/323; 544/325; 544/327; 544/329; 544/334; 544/335; 544/242; 548/131; 548/215; 548/262
[58] Field of Search ............... 544/208, 211, 217, 218, 544/219, 180, 311, 313, 314, 317, 318, 319, 321, 323, 325, 327, 329, 330, 332, 334, 335, 242; 548/131, 215, 262; 252/301.22, 301.23, 301.24

[56] References Cited

U.S. PATENT DOCUMENTS

| | | | |
|---|---|---|---|
| 3,728,399 | 4/1973 | Spacht | 568/47 |
| 3,817,991 | 6/1974 | Meyer et al. | 544/180 |
| 3,830,848 | 8/1974 | Siegrist | 252/301.22 |
| 3,843,633 | 10/1974 | Weber et al. | 252/301.2 |
| 3,850,914 | 11/1974 | Luthi | 252/301.24 |
| 3,880,841 | 4/1975 | Fleck et al. | 548/255 |
| 3,890,305 | 6/1975 | Weber et al. | 548/255 |
| 3,947,410 | 3/1976 | Meyer et al. | 548/143 |
| 3,966,755 | 6/1976 | Schlöpfer | 548/256 |
| 4,008,224 | 2/1977 | Siegrist et al. | 252/301.22 |
| 4,009,193 | 2/1977 | Scheurmann et al. | 252/301.22 |
| 4,032,558 | 6/1977 | Fleck et al. | 260/465 H |
| 4,093,645 | 6/1978 | Davidson et al. | 252/301.22 |
| 4,104,468 | 8/1978 | Valenti | 548/143 |
| 4,323,675 | 4/1982 | Eckes et al. | 548/131 |
| 4,366,189 | 12/1982 | Bardeska et al. | 427/391 |

FOREIGN PATENT DOCUMENTS

| | | |
|---|---|---|
| 0006171 | 6/1979 | European Pat. Off. |
| 0054511 | 12/1981 | European Pat. Off. |
| 0072905 | 6/1982 | European Pat. Off. |
| 3006351 | 9/1981 | Fed. Rep. of Germany |

*Primary Examiner*—John Kight
*Assistant Examiner*—Garnette D. Draper
*Attorney, Agent, or Firm*—Edward McC. Roberts; Meredith C. Findlay; Irving M. Fishman

[57] ABSTRACT

Novel 4-heterocyclylvinyl-4'-styryl-biphenyls of the formula

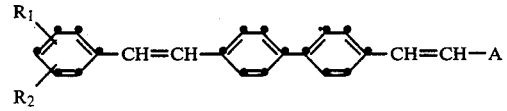

are described, i which A is an isoxazolyl, oxadiazolyl, pyrimidinyl or triazinyl radical which is unsubstituted or substituted by a non-chromophoric substituent, $R_1$ is hydrogen or a non-chromophoric substituent and $R_2$ is hydrogen, halogen, or alkyl; processes for the preparation of these compounds are also described.

The novel 4-heterocyclylvinyl-4'-styryl-biphenyls can be used as fluorescent brighteners for high-molecular organic materials, in particular materials of polyamide and polyester, especially for polyester textiles.

27 Claims, No Drawings

4-HETEROCYCLYLVINYL-4-'STYRYL-BIPHENYLS

The present invention relates to novel 4-heterocyclylvinyl-4'-styryl-biphenyls, to processes for the preparation thereof and to their use for the fluorescent brightening of synthetic, semi-synthetic and natural high-molecular organic materials, and to agents containing these compounds.

Symmetrical 4,4'-bis-(oxadiazolylvinyl)-biphenyls which can be used as fluorescent brighteners for, inter alia, polyesters have been disclosed by U.S. Pat. No. 3,947,410. In practice, these brighteners are suitable mainly for spinning compositions; on textiles, they give only insufficient white effects.

Symmetrical 4,4'-bis-(triazolylvinyl)-biphenyls are also known as fluorescent brighteners. In this connection, see U.S. Pat. No. 3,890,305, U.S. Pat. No. 3,880,841 and U.S. Pat. No. 3,843,633. The two first mentioned United States patents also comprise asymmetrical 4-triazolylvinyl-4'-styrylbiphenyls, but such compounds are not actually described. The 4-triazolylvinyl-4'-styryl-biphenyls described in U.S. Pat. No. 3,843,633 are substituted by at least one sulfo group. They can be used as fluorescent brighteners only on cotton substrates.

The 4-oxadiazolylvinyl-4'-styrylbenzenes which are known from U.S. Pat. No. 4,104,468 and can likewise be used as fluorescent brighteners, in particular for polyesters, should also be mentioned. However, they do not give very high white effects, and their light fastness does not completely satisfy the requirements in practice.

It was the object of the present invention to provide novel compounds which can be used as fluorescent brighteners and which give particularly good brightening effects especially on polyesters and also on polyamide, have good absorption properties and light fastness and do not have the various disadvantages of the above-mentioned known compounds of the state of the art.

Surprisingly, it has been found that certain 4-heterocyclylvinyl-4'-styryl-biphenyls meet these requirements and thus achieve the object of the invention. They also have a particularly high fluorescent brightening yield.

The 4-heterocyclylvinyl-4'-styryl-biphenyls according to the invention are of the formula

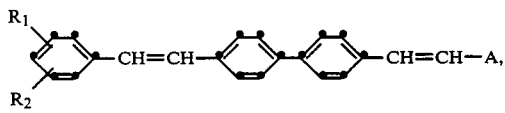

(1)

in which A is an isoxazolyl, oxadiazolyl, pyrimidinyl or triazinyl radical which is unsubstituted or substituted by a non-chromophoric substituent, $R_1$ is hydrogen or a non-chromophoric substituent and $R_2$ is hydrogen, halogen or alkyl.

Non-chromophoric substituents in compounds of the formula (1) are especially those conventional in the fluorescent brightener field. Examples are alkyl or alkoxy, unsubstituted or substituted by a non-chromophoric substituent, alkenyl, cycloalkyl, aryl, aralkyl, pyridyl, substituted or unsubstituted aminocarbonyl and alkoxycarbonyl, cyano, alkylsulfonyl, alkoxysulfonyl, substituted or unsubstituted aminosulfonyl, acyl, acylamino, hydroxyl, alkylmercapto, aryloxy, aralkoxy, alkenyloxy, aryloxycarbonyl, aryloxysulfonyl, aralkoxycarbonyl, carboxyl, sulfo, halogen, acyloxy, trifluoromethyl, amino, mono- or di-alkylamino and alkoxyalkyl.

"Aryl" is preferably to be understood as phenyl which is unsubstituted or substituted by a non-chromophoric substituent, for example phenyl, tolyl or chlorophenyl. In composite groups (for example aryloxy, aralkyl, aralkoxy and the like), aryl has the same preferred definition.

Examples of non-chromophoric substituents for alkyl groups or alkoxy groups are hydroxyl, alkoxy, alkoxyalkoxy, hydroxyalkoxy, halogen, cyano, aryl (in particular phenyl), sulfo, carboxyl, carbalkoxy and aminocarbonyl.

If aryl groups (or aryl groups in composite radicals), in particular phenyl radicals (or phenyl radicals in composite radicals such as phenoxy, phenylalkyl, phenylsulfonyl and the like) are substituted, they preferably carry one or two substituents from the group comprising halogen, in particular chlorine, alkyl and/or alkoxy, and also sulfo or carboxyl and derivatives thereof, cyano and acyl. Preferred substituents are chlorine, methyl and methoxy, of which up to 3 can be present in the ring.

Halogen is especially fluorine, chlorine or bromine, and preferably chlorine.

Acyl is in particular alkylcarbonyl, alkylsulfonyl, and phenylsulfonyl or benzoyl, unsubstituted or substituted by alkyl, alkoxy or halogen.

Alkyl and alkoxy groups as such or in composite groups containing alkyl or alkoxy groups have as a rule 1 to 8, in particular 1 to 6 and preferably 1 to 4, C atoms. Cycloalkyl has preferably 5 or 6 C atoms in the ring. Alkenyl groups have preferably 2 to 6, in particular 3 or 4, C atoms. Alkyl radicals in carboxylate or carboxamide groups or in sulfonamide groups have preferably 1 to 4 C atoms.

"Sulfo" and "carboxyl" are to be understood as meaning the $-SO_3H$ and $-COOH$ groups as well as salts thereof. Preferred salts of these groups are the alkali metal salts and ammonium salts, the latter also including those salts which are derived from organic amines ("amine salts", "substituted ammonium salts"). Sodium and potassium salts are particularly preferred salts.

Preferred substituted aminocarbonyl, alkoxycarbonyl or aminosulfonyl groups are of the formulae $-CONY_1Y_2$, $-COOY_1$ or $-SO_2NY_1Y_2$ respectively, in which $Y_1$ and $Y_2$ independently of one another are hydrogen, alkenyl, cycloalkyl, or alkyl, phenyl or phenylalkyl which are unsubstituted or substituted by a non-chromophoric substituent, or $Y_1$ and $Y_2$, together with the nitrogen atom to which they are linked, are a 5-membered or 6-membered saturated heterocyclic ring which can also contain 1 or 2 additional heteroatoms as ring members and which can be substituted by alkyl groups.

If 5-membered or 6-membered saturated heterocyclic rings ($Y_1+Y_2$) contain still further hetero-atoms in the ring, these can be in particular 1 or 2 nitrogen or/and oxygen atoms. Preferred heterocyclic rings which can be formed by $Y_1$ and $Y_2$ together with the nitrogen atom are the piperidine, piperazine, morpholine, pyrrolidine, imidazolidine and oxazolidine rings.

In preferred 4-heterocyclylvinyl-4'-styryl-biphenyls of the formula (1), $R_1$ is hydrogen or a second-order non-chromophoric substituent. In particularly advantageous compounds of the formula (1), $R_1$ is a second-order non-chromophoric substituent.

Second-order non-chromophoric substituents are the electron-attracting substituents known in organic chemistry, for example acyl radicals of organic carboxylic or sulfonic acids, cyano, trifluoromethyl, the carboxyl and sulfo groups and their functional derivatives, for example their salts, esters and amides, and derivatives of radicals of phosphorus-oxygen compounds.

Acyl radicals are in particular alkylcarbonyl, alkylsulfonyl, and phenylsulfonyl or benzoyl which are unsubstituted or substituted by alkyl, alkoxy or/and halogen. Preferred salts of carboxyl and sulfo groups have already been listed above. Esters of the sulfo group can, for example, be alkoxysulfonyl and phenoxysulfonyl which is unsubstituted or substituted by alkyl, alkoxy and/or halogen. Preferred esters of carboxyl groups or amides of carboxyl and sulfo groups are of the above-defined formulae $COOY_1$ or $CONY_1Y_2$ and $SO_2NY_1Y_2$. An example of derivatives of radicals of phosphorus-oxygen compounds is a group of the formula

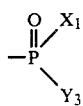

in which $X_1$ and $Y_3$ independently of one another are halogen, alkyl, alkenyl, phenyl, phenylalkyl, hydroxyl, alkoxy, phenylalkoxy, cycloalkoxy, phenoxy, amino, mono- or dialkylamino, phenylalkylamino, acylamino, phenylamino, cycloalkylamino, morpholino, piperidino or pyrrolidino.

In the formulae defined above, the C chains have the chain lengths indicated above as being preferred. Non-chromophoric substituents of alkyl groups are also listed above, as are preferred saturated heterocyclic rings $Y_1+Y_2$.

The substituent A in the compounds of the formula (1) is preferably one of the following heterocyclic rings:

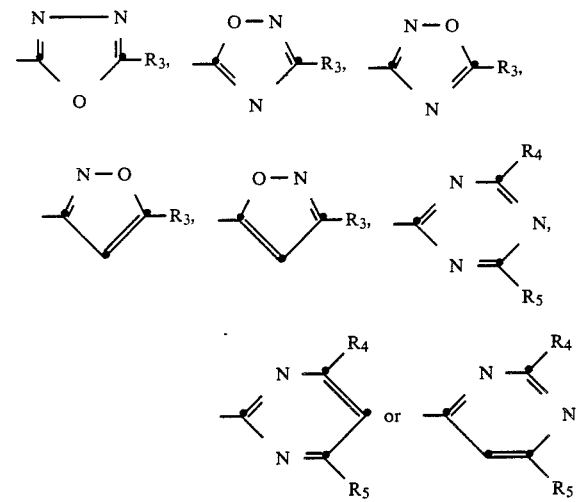

In these formulae, $R_3$, $R_4$ and $R_5$ independently of one another are hydrogen or non-chromophoric substituents. Examples of such substituents have already been given above.

Amongst the 4-heterocyclylvinyl-4'-styryl-biphenyls according to the invention, those of the formula (1) should be mentioned in particular in which $R_1$ is hydrogen, alkylsulfonyl, phenylsulfonyl, alkoxysulfonyl, cyano, trifluoromethyl, a sulfo group and salts thereof, a carboxyl group and salts thereof or a group of the formula $-COOY_1$, $-CONY_1Y_2$ or $-SO_2NY_1Y_2$, in which $Y_1$ and $Y_2$ independently of one another are hydrogen, alkenyl, cycloalkyl, or alkyl or phenylalkyl which are unsubstituted or substituted by a non-chromophoric substituent, or $Y_1$ and $Y_2$, together with the nitrogen atom to which they are linked, are a 5-membered or 6-membered saturated heterocyclic ring which can also contain 1 or 2 additional hetero-atoms as ring members and can be substituted by alkyl groups, $R_2$ is hydrogen, chlorine or alkyl, $R_3$ is hydrogen, alkyl, cycloalkyl, phenyl, benzyl, pyridyl or alkoxyalkyl, and $R_4$ and $R_5$ independently of one another are hydrogen, alkyl, phenyl, alkoxy, halogen, amino, mono- or dialkylamino, alkylmercapto, hydroxyl or alkoxyalkyl.

Preferred non-chromophoric substituents of alkyl groups and saturated nitrogen heterocyclics $(Y_1+Y_2)$ have already been listed above.

Of particular interest are those compounds according to the invention of the formula (1) in which $R_1$ is hydrogen, $C_1$–$C_4$-alkylsulfonyl, phenylsulfonyl, $C_1$–$C_4$-alkoxysulfonyl, cyano, a sulfo group and salts thereof, a carboxyl group and salts thereof or a group of the formula $-COOY_1'$, $-CONY_1'Y_2'$ or $-SO_2NY_1'Y_2'$, in which $Y_1'$ and $Y_2'$ independently of one another are hydrogen, $C_1$–$C_4$-alkyl or benzyl, $R_2$ is hydrogen, chlorine or $C_1$–$C_4$-alkyl, $R_3$ is hydrogen, $C_1$–$C_4$-alkyl, benzyl, phenyl, pyridyl or $C_2$–$C_8$-alkoxyalkyl, and $R_4$ and $R_5$ independently of one another are hydrogen, $C_1$–$C_4$-alkyl, phenyl, $C_1$–$C_4$-alkoxy, chlorine, $C_2$–$C_8$-alkoxyalkyl, $C_1$–$C_4$-alkylmercapto, amino, $C_1$–$C_4$-alkylamino or $C_2$–$C_6$-dialkylamino, and in particular those compounds of the formula (1) in which $R_1$ is hydrogen, $C_1$–$C_4$-alkylsulfonyl, cyano, carboxyl, $C_2$–$C_5$-alkoxycarbonyl or aminocarbonyl, $R_2$ is hydrogen or chlorine, $R_3$ is hydrogen, $C_1$–$C_4$- alkyl, benzyl, phenyl, pyridyl or $C_2$–$C_6$-alkoxyalkyl, and $R_4$ and $R_5$ independently of one another are hydrogen, $C_1$–$C_4$-alkyl, phenyl, $C_1$–$C_4$-alkoxy, $C_1$–$C_4$-alkylmercapto, amino, $C_1$–$C_4$-alkylamino or $C_2$–$C_6$-dialkylamino.

In 4-heterocyclylvinyl-4'-styryl-biphenyls according to the invention which are of particular interest, the substituent A is an unsubstituted or substituted (the substitution being as defined above), 1,3,4-oxadiazol-2-yl, 1,2,4-oxadiazol-5-yl, 1,2,4-oxadiazol-3-yl, 1,2-oxazol-3-yl, 1,2-oxazol-5-yl or 1,3-pyrimidin-2-yl radical, and preferably a 1,3,4-oxadiazol-2-yl, 1,2,4-oxadiazol-5-yl or 1,2,4-oxadiazol-3-yl radical.

Preferred 4-heterocyclylvinyl-4'-styryl-biphenyls according to the invention are of the formula

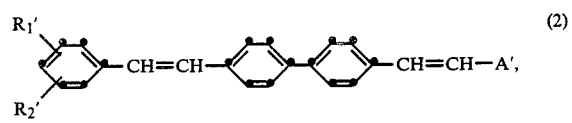

(2)

in which $R_1'$ is $C_1$–$C_4$-alkylsulfonyl, cyano, carboxyl or $C_2$–$C_5$-alkoxycarbonyl, $R_2'$ is hydrogen or chlorine and A' is a radical of the formula

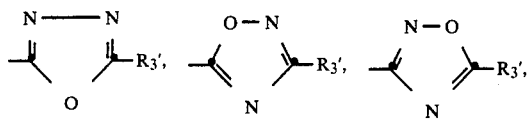

in which $R_3'$ is hydrogen, $C_1$-$C_4$-alkyl or phenyl, preferably $C_1$-$C_4$-alkyl.

Those from all the abovementioned 4-heterocyclylvinyl-4'-styryl-biphenyls according to the invention are of very particular practical interest in which the substituent $R_1$ or $R_1$ is cyano, $C_1$-$C_4$-alkylsulfonyl or $C_2$-$C_5$-alkoxycarbonyl, and preferably cyano, and $R_2$ or $R_2'$ is hydrogen.

The 4-heterocyclylvinyl-4'-styryl-biphenyls of the formula (1) according to the invention, and hence also the preferred compounds covered by this formula, can be obtained by various processes known per se.

One process for preparing the compounds of the formula (1) comprises reacting a compound of the formula

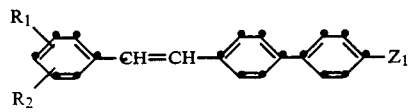
(3)

with a compound of the formula $Z_2$-A, or reacting a compound of the formula

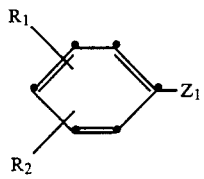
(4)

with a compound of the formula

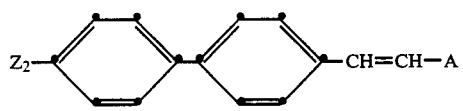
(5)

$R_1$, $R_2$ and A in the above formulae being as defined in formula (1) and one of the two substituents $Z_1$ and $Z_2$ in each case being the group

and the other being methyl, carboxymethyl (or a functional derivative thereof) or a group of the formula

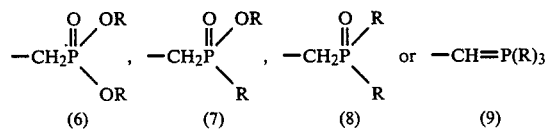

in which R is unsubstituted or substituted $C_1$-$C_5$-alkyl or unsubstituted or substituted phenyl.

Examples of functional derivatives of the carboxymethyl group are the groups of the formulae —$CH_2CN$, —$CH_2$—$CONH_2$, —$CH_2COCl$ or —$CH_2COOR'$, in which R' is $C_1$-$C_4$-alkyl. If functional derivatives of the carboxymethyl group are used, it can be necessary, depending on the reaction conditions, to follow the main reaction with a saponification step involving decarboxylation.

The condensation of a compound of the formula (3) with a compound of the formula $Z_2A$, or of a compound of the formula (4) with a compound of the formula (5), can generally be carried out in the melt, but preferably in an inert solvent at temperatures between 20° and 150° C., if necessary in the presence of a catalyst. Examples of solvents are hydrocarbons, such as toluene and xylene, or alcohols, such as methanol, ethanol, isopropanol, butanol, glycol, glycol ethers such as 2-methoxyethanol, hexanols, cyclohexanols and cyclooctanol, and also ethers, such as diisopropyl ether, tetrahydrofuran and dioxan. Polar organic solvents, such as dimethylformamide, N-methylpyrrolidone and dimethyl sulfoxide, are particularly suitable. Some of the reactions can also be carried out in aqueous solutions. Examples of suitable catalysts are tertiary amines, such as pyridine, picoline, triethylamine and piperidine, zinc chloride, boric acid, boric anhydride, acetic anhydride, p-toluenesulfonic acid, and also alkali metal acetates, alkali metal hydroxides or alkaline earth metal hydroxides, alkali metal alcoholates, potassium phthalimide and potassium carbonate.

If one of the substituents $Z_1$ or $Z_2$ is a methyl group of a carboxymethyl group or a derivative thereof, the condensation can also be carried out, for example, as described in U.S. Pat. No. 4,032,558 or U.S. Pat. No. 3,728,339. Accordingly, it is advantageously carried out in the presence of basic catalysts under the conditions of the Knoevenagel reaction. Since the reactivities of both the aldehyde group and the methyl or methylene group vary as a function of the particular substituents, the reaction conditions must be adapted accordingly. The reaction is carried out in the range from 75° to 200° C., without or with solvents which, if desired, enable the water of reaction to be removed azeotropically. Examples are: benzene, chlorobenzene, toluene, xylene, pyridine, acetic acid and DMF. Suitable basic catalysts are, inter alia, sodium benzenesulfonamide, potassium carbazole, ammonium acetate, and in particular organic nitrogen bases, such as dibutylamine, dibenzylamine, morpholine, hexamethyleneimine and preferably piperidine. The reaction is complete when the evolution of $CO_2$ ceases.

If one of the substituents $Z_1$ or $Z_2$ is a phosphorus-containing group of the formulae (6)–(9), the reaction is advantageously carried out under the conditions of the Wittig-Horner synthesis. In this synthesis, the solvent used is advantageously an inert solvent, for example a hydrocarbon, such as toluene or xylene, or an alcohol such as methanol, ethanol, isopropanol, butanol, glycol, a glycol ether such as 2-methoxyethanol, hexanol, cyclohexanol or cyclooctanol, or an ether such as diisopropyl ether, dioxane or tetrahydrofuran, or also formamide or N-methylpyrrolidone. Dipolar organic solvents such as dimethylformamide and dimethyl sulfoxide are particularly suitable.

Preferably, condensation agents are used. These can be, for example, strongly basic compounds, such as alkali metal and alkaline earth metal hydroxides, alkali metal and alkaline earth metal amides and alkali metal and alkaline earth metal alcoholates, for example potassium hydroxide, sodium hydroxide, potassium tert.-butylate, sodium amide or sodium methylate, and also the alkali metal compounds of dimethyl sulfoxide and alkali metal hydrides as well as, in some cases, alkali metal dispersions.

The reaction is preferably carried out in the temperature range from 0° to 100° C. The compounds according to the invention are also obtained if, in place of phosphono compounds, the corresponding quaternary phosphonium salts, for example the triphenylphosphonium salts, are used and these are condensed with the aldehydes via the phorphorylene stage.

Further conversions known per se can be carried out with the reaction product of the above processes, such as functional modifications of carboxyl and sulfo groups, for example transesterifications or exchanges of halogen atoms for cyano groups. The conversion of carboxylates into carbonamides by condensation with ammonia or amines is of particular importance.

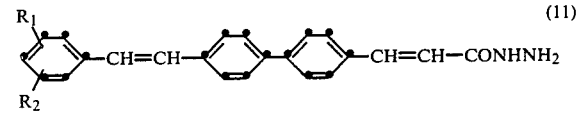

with a carboxylic acid of the formula HOOC—R$_3$ or a functional derivative of this acid, R$_1$ and R$_2$ being as defined in formula (1) and R$_3$ being as defined above, and cyclising the condensation product obtained in the presence of a dehydrating agent.

Examples of functional derivatives of carboxylic acids, which can be used, are carboxylic acid halides, such as chlorides and bromides, carboxylic acid anhydrides, carboxylates such as alkylcarboxylates having 1-4 C atoms in the alkyl group, carboxamides and nitriles. Carboxylic acid chlorides are preferred.

In the first stage of the reaction, a hydrazine compound of the formula

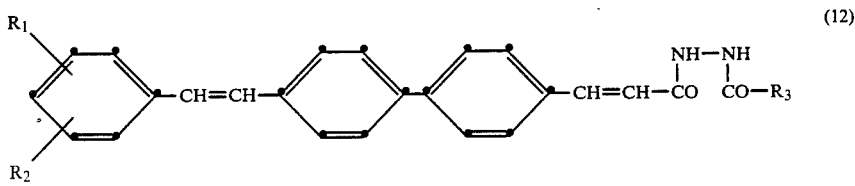

The aldehydes of the formula (3) to (5) and Z$_2$-A (Z$_1$, Z$_2$=CHO) are known or can readily be obtained by known processes. Some of these aldehydes, in particular those of the formula (3) are known from EP No. 54,511. Aldehydes not described therein can be obtained in an analogous manner in accordance with the instructions given there or in the examples of this application. Aldehydes with R$_1$=carboxyl are also obtained by, preferably acidic, hydrolysis of the corresponding carboxylates.

The phosphorus compounds (Z$_1$, Z$_2$=groups of the formulae (6)–(9), in particular those of the formula Z$_2$-A, are known, for example from DE No. 3,006,351, or can readily be obtained by the processes indicated there. See also EP No. 31,796.

A further process for the preparation of compounds of the formula (1), in which A is a group of the formula

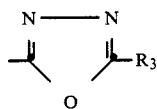

and R$_3$ is a hydrogen or a non-chromophoric substituent, comprises reacting a carboxylic acid of the formula

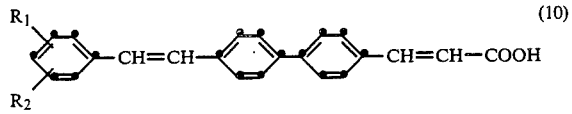

or a functional derivative of this acid with a carboxylic acid hydrazide of the formula H$_2$N—NH—CO—R$_3$, or reacting a compound of the formula is formed. This compound can be isolated, or the second stage (cyclisation) can follow directly without isolation of the compound.

The reaction of the acid (10) with the hydrazide NH$_2$NH—CO—R$_3$, or of the acid HOOC—R$_3$ with the hydrazide (11) can be carried out by heating to temperatures above 100° C., advantageously to 120° to 300° C., advantageously in the presence of an inert organic solvent, such as toluene, xylenes, chlorobenzene, dichlorobenzenes, trichlorobenzene or nitrobenzene, or, if acid chlorides are used, preferably in the presence of a catalytically active or acid-accepting agent, for example in pyridine bases, such as picolines or pyridine, other tertiary amines, such as triethylamine, or alkali metal hydroxides, at 0°–120° C. The conversion into the oxadiazolyl compound (cyclisation) takes place, as a rule, by treatment of the diacylhydrazine compound of the formula (12) with dehydrating agents, such as phosphorus oxychloride, phosphorus trichloride, phosphorus pentachloride, phosphorus pentoxide, polyphosphonic acid, sulfuric acid, sulfuryl chloride, oleum/dimethylformamide, zinc chloride, aluminum chloride, p-toluenesulfonic acid or thionyl chloride, at temperatures between 100° and 250° C. If desired, high-boiling organic solvents, for example dimethylformamide, dichlorobenzene, trichlorobenzene, nitrobenzene, pyridine and aliphatic hydroxy compounds, which may be etherified, for example propylene glycol, ethylene glycol monoethyl ether, diethylene glycol diethyl ether or diethylene glycol dibutyl ether, can also be used additionally.

In a particularly advantageous embodiment, an acid halide, preferably the chloride, of the acid of the formula (10) is reacted with a hydrazide of the formula H$_2$NNH—CO—R$_3$, preferably in the presence of a catalytically active or hydrogen halide-binding agent, and the acylhydrazine compound obtained is subjected to an oxadiazole cyclisation reaction by treatment with a dehydrating agent, for example phosphorus oxychloride, between 100° and 200° C.

For the preparation of compounds according to the invention, of the formula (1), in which A is a group of the formula

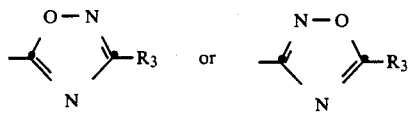

(with $R_3$=hydrogen or a non-chromophoric substituent), the procedure can be such that a carboxylic acid of the formula

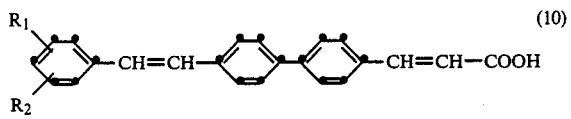

or a functional derivative of this acid is reacted with an amidoxime of the formula

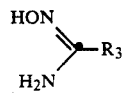

or a compound of the formula

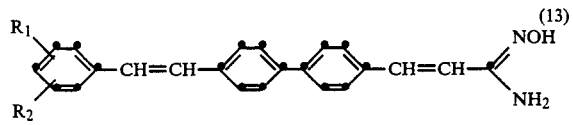

is reacted with a carboxylic acid of the formula HOOC—$R_3$ or a functional derivative of this acid, $R_1$ and $R_2$ being as defined in formula (1) and $R_3$ being defined above, and the condensation product obtained is cyclised in the presence of a dehydrating agent.

For example, carboxylic acid halides, such as chlorides and bromides, carboxylic acid anhydrides, carboxylic acid esters, such as alkylcarboxylates having 1–4 C atoms in the alkyl group, carboxamides and nitriles can be used as functional derivatives of the carboxylic acids. Carboxylic acid chlorides are preferred.

The first stage (reaction of an acid or a derivative thereof with an amidoxime) can, for example, be carried out in the presence of an acid acceptor (if, for example, a carboxylic acid halide is used). Preferred reaction temperatures are 0°–80° C. The acylation products formed can be isolated; preferably, however, the cyclisation is carried out without isolation of the intermediate. The cyclisation can be carried out, for example, by heating to 100°–200° C., preferably 160°–200° C., preferably with removal of the water formed, by azeotropic distillation with a suitable solvent.

Examples of suitable solvents for the reaction are toluene, xylene, ethylene chloride, chlorobenzene, dichlorobenzene or trichlorobenzene, and in particular dimethylformamide, N-methylpyrrolidone, dimethyl sulfoxide or nitrobenzene. Examples of acid acceptors are $Na_2CO_3$, $K_2CO_3$, $CaCO_3$ or tertiary amines, for example pyridine, triethylamine or N,N-dimethylaniline.

The starting products required in the two last-mentioned processes (compounds of the formulae (10), (11), (13), $H_2NNH$—CO—$R_3$, HOOC—$R_3$ and

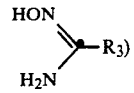

are known or can by prepared by processes known per se. In this connection, see EP No. 6,171, U.S. Pat. No. 4,323,675, EP No. 72,905 and U.S. Pat. No. 3,947,410

In the dissolved or finely divided state, the 4-heterocyclylvinyl-4'-styryrl-biphenyls according to the invention, of the formula (1), show a pronounced fluorescence. They can be used for fluorescent brightening of the most diverse synthetic, semi-synthetic or natural high-molecular organic materials. This use is also a subject of the present invention.

Examples of materials to be brightened are the following groups of organic materials, inasmuch as fluorescent brightening is applicable to them; the list which follows is not intended to imply any restriction thereto.

1. Synthetic organic high-molecular materials:

(a) polymerisation products based on organic compounds containing at least one polymerisable carbon-carbon double bond, i.e. their homopolymers or copolymers, and their after-treatment products, for example crosslinked products, graft products or degradation products, polymer blends, or products obtained by modification of reactive groups, for example polymers based on $\alpha,\beta$-unsaturated carboxylic acids or derivatives of such carboxylic acids, in particular acrylic compounds (for example acrylates, acrylic acid, acrylonitrile, acrylamides and their derivatives or their methacrylic analogues), olefin hydrocarbons (for example ethylene, propylene, styrene or dienes, also so-called ABS polymers), and polymers based on vinyl and vinylidene compounds (for example vinyl chloride, vinyl alcohol or vinylidene chloride), (b) polymerisation products which are obtainable by ring-opening, for example polyamides of the polycaprolactam type, and also polymers which are obtainable either by polyaddition or by polycondensation, such as polyethers or polyacetals, (c) polycondensation products or precondensates based on bifunctional or polyfunctional compounds with condensable groups, their homocondensation and cocondensation products and after-treatment products, for example polyesters, in particular saturated polyesters (for example ethylene glycol terephthalate polyesters) or unsaturated polyesters (for example maleic acid/dialcohol polycondensates and their cross-linked products with copolymerisable vinyl monomers), unbranced and branched polyesters (also including those based on polyhydric alcohols, for example alkyd resins), polyamides (for example hexamethylenediamine adipate), maleate resins, melamine resins, their precondensates and analogues, polycarbonates and silicones.

(d) polyaddition products, such as polyurethanes (crosslinked and uncrosslinked) and epoxide resins.

II. Semi-synthetic organic materials, for example cellulose esters or different degrees of esterification (so-called 2½ acetate, triacetate) or cellulose ethers, regenerated cellulose (viscose, cuprammonium cellulose) or their after-treatment products, and casein plastics.

III. Natural organic materials of animal or vegetable origin, for example those based on cellulose or proteins, such as cotton, wool, linen, silk, natural lacquer resins, starch and casein.

The organic materials which are to undergo fluorescent birghtening can be in the most diverse processing states (raw materials, semi-finished articles or finished articles). They can also be in the form of the most diverse shaped structures, i.e. for example predominantly three-dimensional bodies, such as plates, profiles, injection mouldings, various workpieces, chips, granules or foams, and also predominantly two-dimensional bodies, such as films, sheets, lacquers, coatings, impregnations and layers, or predominantly uni-dimensional bodies, such as filaments, fibres, flocks and wires. On the other hand, the said materials can also be in unshaped states in the most diverse homogeneous or inhomogeneous forms of distribution, for example powders, solutions, emulsions, dispersions, latices, pastes or waxes.

Fibre materials can, for example, be in the state of continuous filaments (stretched or unstretched), staple fibres, flocks, hanks, textile fibres, yarns, twisted yarns, nonwovens, felts, wadding, flocked structures, or textile fabrics or textile composites, knitted products, and papers, cardboards or paper pulps.

The compounds of the formula (1), which are to be used according to the invention, are important in particular for the treatment of textile organic materials, especially textile fabrics. If fibres, which can be in the form of staple fibres or continuous filaments in the form of hanks, woven fabrics, knitted fabrics, nonwovens, flocked substrates or composites, are to be subjected to fluorescent brightening according to the invention, this is advantageously in an aqueous medium, which contains the compounds concerned in a finely divided form (suspensions, so-called microdispersions and, if appropriate, solutions). If appropriate, dispersing agents, stabilisers, wetting agents and other auxiliaries can be added during the treatment.

The application can take place in a neutral, alkaline or acidic bath. The treatment is usually carried out at temperatures from about 20° to 140° C., for example at the boiling point of the bath or in the vicinity thereof (about 90° C.). For the finishing, according to the invention, of textile substrates, solutions or emulsions in organic solvents can also be used, as is conventional in dyeing practice in so-called solvent dyeing (pad-thermofixing application, exhaustion dyeing process in dyeing machines).

The fluorescent brighteners according to the present invention can also be added, to, or incorporated in, the materials before or during their shaping. Thus, for example in the production of films, sheets (for example hot milling into polyvinyl chloride) or mouldings, they can be added to the compression-moulding composition or injection-moulding composition.

If fully synthetic or semi-synthetic organic materials are shaped by spinning processes or via spinning compositions, the fluorescent brighteners can be applied by the following processes:

addition to the starting substances (for example monomers) or intermediates (for example precondensates or prepolymers), i.e. before or during the polymerisation, polycondensation or polyaddition, sprinkling a powder onto polymer chips or granules for spinning compositions, bath dyeing of polymer chips or granules for spinning compositions, metered addition to spinning melts or spinning solutions, application to tows before stretching.

The fluorescent brighteners according to the invention can also be used, for example, in the following application forms:

(a) as mixtures with dyes (shading) or pigments (coloured pigments or especially, for example, white pigments), or as an addition to dye baths, printing pastes, discharge pastes or reserve pastes, and also for the aftertreatment of dyeings, prints or discharge prints, (b) as mixtures with so-called "carriers", wetting agents, plasticisers, swelling agents, antioxidants, light stabilisers, heat stabilisers and chemical bleaches (chlorite bleach, bleach bath additives), (c) as a mixture with crosslinking agents, finishing agents (for example starch or synthetic finishes) and in combination with the most diverse textile finishing processes, in particular synthetic resin finishes (for example crease-resistant finishes, such as "wash-and-wear", "permanent-press", "non-iron"), and also flameproofing finishes, soft handle finishes, anti-soiling finishes or antistatic finishes or antimicrobial finishes, (d) incorporation of the fluorescent brightening agents into polymeric carrier materials (polymerisation, polycondensation or polyaddition products) in a dissolved or dispersed form for use, for example, in coating agents, impregnating agents or binders (solutions, dispersions, emulsions) for textiles, nonwovens, paper or leather, (e) as additives to the most diverse industrial products to make these more marketable (for example improvement of the appearance of soaps, detergents, pigments), (f) in spinning bath preparations, i.e. as additives to spinning baths, such as are used to improve the slip for the further processing of synthetic fibres, or from a special bath before the fibre is stretched, (g) in agents for fluorescent brightening of high-molecular organic materials of the compositions given above, which agents can, if appropriate, contain conventional formulation additives and/or further fluorescent brighteners from other brightener classes, (h) in combination with other substances having a fluoroscent brightening effect; and also as additives to so-called master batches, (i) as scintillators for various purposes of a photographic nature, for example for electrophotographic reproduction and super-sensitisation, (j) depending on the substitution, as laser dyes.

Agents which contain the fluorescent brighteners according to the invention of the formula (1) are also a subject of the invention.

Conventional formulation additives which can be present in such agents are, for example, the most diverse auxiliaries and extenders, such as anhydrous sodium sulfate, sodium sulfate decahydrate, sodium chloride, sodium carbonate, alkali metal phosphates, such as sodium or potassium orthophosphates, sodium or potassium pyrophosphate and sodium or potassium tripolyphosphates, or alkali metal silicates. However, the agents according to the invention also include aqueous formulations, for example also the application solutions by means of which textile fibres are fluorescently brightened and which contain the conventional additives.

A further subject of the invention is agents which, in addition to one or more compounds of the formula (1), also contain one or more fluorescent brighteners from the group comprising he triazinyl-pyrenes, 2-styryl-benzoxazoles, 1,4-bis-styrylbenzenes, 4-benzoxazolylstilbenes, 4,4'-divinylstilbenes, naphthalimides, 4,4'-bis-styrylbiphenyls, 4,4'-bis-triazolylstilbenes, bis-benzoxazolyl-thiophenes, -naphthalenes or -ethylenes, oxadiazolylstilbenes, naphthotriazol-2-yl-stilbenes (for example known from U.S. Pat. No. 4,172,045) or coumarins, for example triazolyl-coumarins (known from U.S. Pat. No. 3,966,755) and pyrazolyl coumarins, or consist of such brightener combinations. Those agents are preferred which, as the active brightener substance, contain 10–99%, in particular 30–70%, of a fluorescent brightener according to the invention, of the formula (1), and 90–1%, in particular 70–30%, of a fluorescent brightener from the abovementioned classes. Such combinations of fluorescent brighteners do not have to contain further additives, i.e. they can be pure brightener mixtures. Preferably, the brighteners from the abovementioned classes in the brightener combinations according to the invention are polyester brighteners.

Such combinations have the advantage that a particularly attractive neutral white shade of high brilliance can be achieved on textile fibres, especially on polyester fibres.

Fluorescent brighteners which are particularly important in practice and which can be used together with the compounds according to the invention, of the formula (1), in the abovementioned brightener combinations, are inter alia:

4-chloro-2'-cyano-4'-(naphthotriazol-2-yl)-stilbene, 3-phenyl-7-(3'-methylpyrazol-1-yl)-coumarin, 4-(pyrimidin-2-yl)-4'-(cyanovinyl)-stilbene, 1-(4'-cyanophenyl)-2-(5',6'-dimethylbenzoxazol-2'-yl)-ethylene, 3-phenyl-7-(4'-phenyl-5'-methyl-v-triazol-2-yl)-coumarin, 3-(4'-chloropyrazol-1'-yl)-7-(4'-phenyl-5'-methyl-v-triazol-2-yl)-coumarin, 1-methyl-5,6-diethoxynaphthalimide, 1-methyl-5-methoxynaphthalimide, 3-phenyl-7-naphthotriazol-2'-yl-coumarin and in particular 1,4-bis-(benzoxazol-2-yl)-naphthalene, 1-(4'-methoxycarbonylphenyl)-2-(5',6'-dimethylbenzoxazol-2'-yl)-ethylene, 4,4'-bis-(ethoxycarbonyl-vinyl)-stilbene, 4,4'-bis-(cyano-vinyl)-stilbene, 1,4-bis-(2'-cyanostyryl)-benzene, 2,5-bis-(benzoxazol-2'-yl)-thiophene, 4-phenyl-4'-(5'',7''-di-methylbenzoxazol-2''-yl)-stilbene, 1,2-bis-(5'-methyl-benzoxazol-2'-yl)-ethylene, 4-(benzoxazol-2'-yl)-4'-(3''-methyl-1'',2'',4''-oxadiazol-5''-yl)-stilbene or 2,4-dimethoxytriazin-6-yl-pyrene.

The quantitative ratio of the abovementioned brighteners and the particular 4-heterocyclylvinyl-4'-styrylbiphenyls of the formula (1) in particular preferred brighttener mixtures ranges from 1:2 to 2:1.

Particularly preferably, substrates or polyester, in particular textile materials of polyester, are brightened with the fluorescent brighteners according to the invention, which do not contain any sulfo groups. However, polyamide and other synthetic fibres can also be brightened with very good effect. Compounds of the formula (1), which contain sulfo groups, can also be used for the fluorescent brightening of cellulose, in particular cotton textiles. Mixtures of compounds of the formula (1) which do and do not contain sulfo groups, are thus suitable also for the brightening of mixed polyester/cotton fibres.

If the brightening process is combined with textile treatment or finishing methods, the combined treatment can in many cases be advantageously carried out by means of appropriate stable preparations which contain the fluorescent brightener compounds in such a concentration that the desired brightening effect is obtained.

In certain cases, the full effect of the brighteners is obtained by an after-treatment. This can be, for example, a chemical treatment (for example an acid treatment), a thermal treatment or a combined chemical/thermal treatment. Thus, for example, for fluorescent brightening of a number of fibre substrates, for example polyester fibres, with the brighteners according to the invention, the procedure is advantageously such that these fibres are impregnated with the aqueous dispersions (or also solutions, as appropriate) of the brighteners at temperatures below 75° C., for example at room temperature, and are subjected to a dry heat treatment at temperatures above 100° C., it being advisable in general also to dry the fibre material beforehand at a moderately elevated temperature, for example from at least 60° C. up to about 130° C. The heat treatment in the dry state is then advantageously carried out at temperatures between 120° and 225° C., for example by heating in a drying chamber, by ironing within the indicated temperature interval or by treatment with dry superheated steam. The drying and the dry heat treatment can also be carried out in immediate succession or they can be combined in a single working step.

The quantity of the fluorescent brighteners to be used according to the invention, relative to the material which is to be fluorescently brightened, can vary within wide limits. A marked and durable effect can be achieved with very small quantities, for example 0.001 percent by weight in certain cases. However, quantities up to about 0.8 percent by weight and, if necessary, up to about 2 percent by weight can also be applied. For most practical aspects, preferably quantities between 0.01 and 0.5 percent by weight are of interest.

Particularly preferred fields of application of the compounds according to the invention are the following:

Fluorescent brightening of polyester, and in particular both polyester fibres and polyester fabrics by the exhaustion process or pad-bake process, and of polyester spinning compositions. Mixed fabrics of polyester and cotton or wool are also very advantageously brightened by means of the compound according to the invention. Examples of further substrates which can advantageously be brightened by means of the compounds of the formula (1) are: polyamide fibre fabrics, cellulose acetate fabrics, and polystyrene and polyvinyl chloride compositions. However, the use for fluorescent brightening of polyester fibres by the exhaustion process and pad-bake process is particularly preferred.

The compounds according to the invention, of the formula (1), in particular those which contain sulfo groups as substituents, are also especially suitable as additives for washing baths or commercial and domestic detergents, in which cases they can be added in various ways. Advantageously, they are added to washing baths in the form of their solutions in water or organic solvents, or in fine distribution as aqueous dispersions. They are advantageously added to domestic or commercial detergents during any phase of the detergent manufacturing process, for example the so-called slurry before atomisation of the washing powder, or during the preparation of liquid detergent combinations. They can be added either in the form of a solution or dispersion in water or other solvents, or without auxiliaries as a dry brightener powder. For example, the brightening agents can be mixed, kneaded or ground with the washing-active substances, and can be admixed to the finished washing powder in this way. However, they can also be sprayed in a dissolved or predispersed form on to the finished washing agent.

The washing agents can be the known mixtures of washing-active substances, for example soaps in the form of chips and powder, synthetics, soluble salts of sulfonic acid half-esters of higher fatty alcohols, arylsulfonic acids substituted by higher alkyl and/or polysubstituted by alkyl, sulfocarboxylic acid esters of medium to higher alcohols, fatty acid acylaminoalkyl- or -aminoaryl-glycerol-sulfonates, phosphoric acid esters of fatty alcohols and the like. The builders used can be, for example, alkali metal polyphosphates and polymetaphosphates, alkali metal pyrophosphates, alkali metal salts of carboxymethylcellulose and other soil-redeposition inhibitors, and also alkali metal silicates, alkali metal carbonates, alkali metal borates, alkali metal perborates, nitrilotriacetic acid, ethylenediaminetetraacetic acid and foam stabilisers such as alkanolamides of higher fatty acids. The washing agents can also contain, for example, antistatic agents, superfatting skin protectives such as lanolin, enzymes, antimicrobial agents, perfumes and dyes.

The compounds according to the invention have the particular advantage that they are effective also in the presence of active chlorine donors, for example hypochlorite, and can be used, without significant loss of effect, in washing baths with non-ionic washing agents, for example alkylphenol polyglycol ethers.

The compounds according to the invention are added in quantities of 0.005 to 1% or more, relative to the weight of the liquid or pulverulent finished washing agent. Washing liquors which contain the indicated quantities of the claimed brighteners impart a brilliant aspect in daylight to textiles consisting of cellulose fibres, polyamide fibres, highly improved cellulose fibres, polyester fibres, wool and the like, when these are washed.

The washing treatment is carried out, for example, as follows:

The textiles indicated are treated for 1 to 30 minutes at 20° to 100° C. in a washing bath which contains 1 to 10 g/kg of a built composite washing agent and 0.05 to 1%, relative to the weight of the washing agent, of the claimed brighteners. The liquor ratio can be 1:3 to 1:50. After washing, the goods are rinsed and dried in the usual way. As a bleach additive, the washing bath can contain 0.2 g/l of active chlorine (for example as hypochlorite) or 0.1 to 2 g/l of sodium perborate.

The examples which follow further illustrate the preparation of the compounds according to the invention and their use. In these examples, in the same way as in the remainder of the description, percentage and parts data are always by weight, unless otherwise stated. Melting points and boiling points are uncorrected, unless otherwise stated.

EXAMPLE 1

5.4 g of a 30% solution of sodium methylate in methanol are added dropwise with stirring after the air has been displaced by nitrogen, to a mixture of 6.2 g of 4-(2-cyanostyryl)-biphenyl-4'-aldehyde and 7.4 g of the compound of the formula

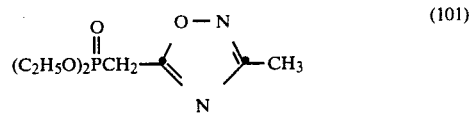 (101)

(content: 70.1%) in 80 ml of dimethylformamide, in such a way that the temperature does not rise above 40° C. The temperature is held for 2 hours at 40°–45° C., the reaction mixture is cooled with ice water and 80 ml of water are added. The precipitated product is filtered off with suction, washed repeatedly with methanol and water and dried in vacuo at 100° C. This gives 7.0 g of the compound of the formula

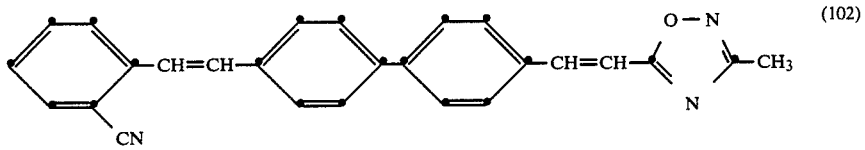 (102)

in the form of light yellow crystals having a melting point of 178°–180° C. (after one recrystallisation from xylene).

The compounds listed in Table 1, of the formula

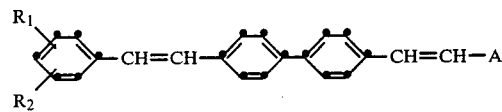

are obtained analogously from the appropriately substituted 4-styrylbiphenyl-4'-aldehydes and the heterocyclylmethylphosphonates of the type of formula (101).

TABLE 1

| Formula | $R_1$ | $R_2$ | A | Melting point (°C.) |
|---|---|---|---|---|
| 103 | 4-CN | H | 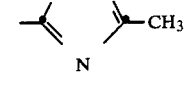 | 237 |
| 104 | 4-CN | H | 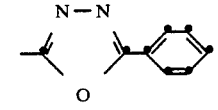 | 266 |
| 105 | 4-CN | H | 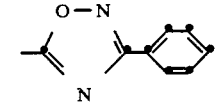 | 241 |
| 106 | 4-CN | H | 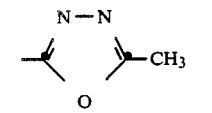 | 237 |
| 107 | 4-CN | H | 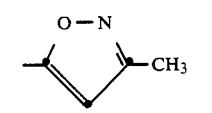 | 251 |

TABLE 1-continued

| Formula | R₁ | R₂ | A | Melting point (°C.) |
|---|---|---|---|---|
| 108 | 2-CN | H | (N—N, O, phenyl-fused) | 229 |
| 109 | 2-CN | H | (O—N, N, phenyl-fused) | 188 |
| 110 | 4-COOH | H | (N—N, O, —C₂H₅) | about 320 |
| 111 | 4-CN | H | (N—O) | 260 |
| 112 | 2-CN | H | (O—N, phenyl-fused) | 236 |
| 113 | 4-CN | H | (N—N, O, —C₂H₅) | 219 |
| 114 | 4-CN | H | (O—N, N, —C₂H₅) | 189 |
| 115 | 2-CN | H | (N—N, O, —C₂H₅) | 180 |
| 116 | 2-CN | H | (O—N, N, —C₂H₅) | 165 |
| 117 | 2-CN | H | (N—N, O, —CH₃) | 210 |
| 118 | 2-CN | H | (O—N, —CH₃) | 193 |
| 119 | 4-COOC₂H₅ | H | (N—N, O, —CH₃) | 281 |
| 120 | 4-CN | 3-Cl | (O—N, N, —CH₃) | 237 |
| 121 | 4-CN | H | (N—O, —CH₃) | 282 |
| 122 | 4-SO₂CH₃ | H | (O—N, N, —C₂H₅) | 317 |
| 123 | 3-CN | H | (N—N, O, phenyl-fused) | 227 |
| 124 | H | H | (N—N, O, —C₂H₅) | about 260 |

4-(4-methylsulfonylstyryl)-biphenyl-4'-aldehyde of the formula

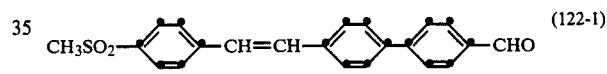
(122-1)

which is required for the preparation of the compound of the formula (122) is obtained as follows: 34.7 g of a 30% solution of sodium methylate in methanol and then, in the course of one hour, a solution of 35.2 g of the phosphonate of the formula

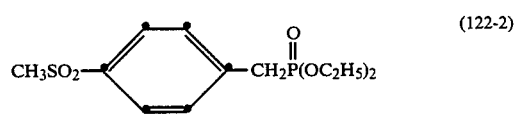
(122-2)

(content: 87%) in 50 ml of methanol are added, at room temperature and with stirring and introduction of nitrogen, to a suspension of 21.0 g of biphenyl-4,4'-dialdehyde in 200 ml of methanol. After further stirring for 20 hours at room temperature, the reaction product is filtered off with suction, washed repeatedly with methanol and dried. For purification, it is extracted overnight with hot methylene chloride in a Soxhlet apparatus, and the evaporated extract is stirred up in methanol and filtered off with suction. After drying in vacuo at 100° C., this gives 26.3 g of a pale yellow product. This can be recrystallised from ethylene glycol monomethyl ether, and it has a melting point of 243° C.

Most of the other starting compounds of the formula (3) ($Z_1$=CHO) can be prepared by this process, unless they are anyway known from the literature.

The aldehyde of the formula

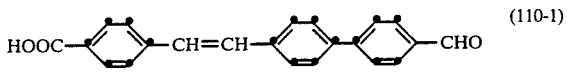 (110-1)

(melting point about 310° C.) required for the preparation of the compound of the formula (110) is obtained, for example, by saponifying the corresponding acyl ester in a mixture of dioxane and concentrated hydrochloric acid in a volume ratio of 6:1 at reflux temperature.

The 4'-styryl-biphenyl-4-aldehyde required for the preparation of the compound of the formula (124) is obtained, for example, by reacting 4,4'-biphenyl-dialdehyde with benzyl-triphenyl-phosphonium chloride in the presence of sodium methylate in methanol, by the Wittig method.

EXAMPLE 2

6.7 g of potassium tert.-butylate are added, with stirring and introduction of nitrogen, to a solution of 9.3 g of 4-(4-cyanostyryl)-biphenyl-4'-aldehyde and 3.2 g of 2-methyl-pyrimidine (concentration: 94%) in 100 ml of dimethylformamide. After stirring for 2 hours at 50° C., the mixture is cooled in an ice bath, and 70 ml of water are added. The precipitated product is filtered off with suction, washed repeatedly with methanol and water, dried in vacuo at 100° C. and recrystallised from o-dichlorobenzene. This gives 4.9 g of a light yellow, crystalline product of the formula

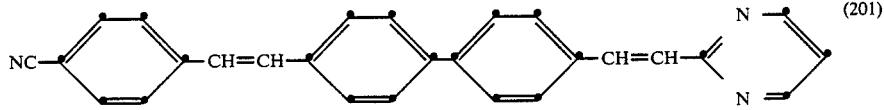

having a melting point of 309° C.

The procedure described above is repeated, except that the same quantity of 4-(2-cyanostyryl)-biphenyl-4'-aldehyde is used in place of the aldehyde indicated, affording the compound of the formula

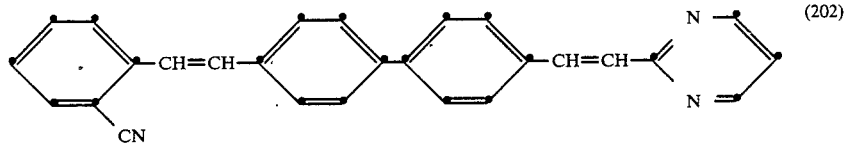 (202)

having a melting point of 220° C., after recrystallisation from ethylene glycol monomethyl ether and xylene.

The compounds of the formula

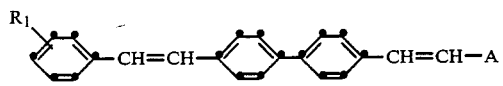

listed in Table 2 are obtained analogously, using the appropriately substituted starting products.

TABLE 2

| Formula | R₁ | A | |
|---------|------|---|---|
| 203 | 2-CN | (pyrimidine) | 187 |
| 204 | 2-CN | (4,6-dimethylpyrimidine) | 214 |
| 205 | 2-CN | (2,6-dimethylpyrimidine) | 195 |
| 206 | 4-CN | (2,6-dimethylpyrimidine) | 264 |

EXAMPLE 3

The procedure described in Examples 1 and 2 is repeated, except that the appropriately substituted starting products are used, affording the compounds of the formula

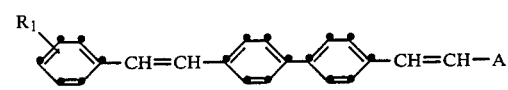 (201)

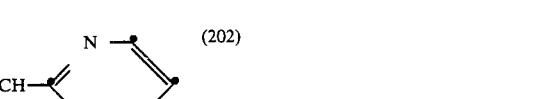

listed in Table 3.

TABLE 3

| Formula | R₁ | A |
|---------|------|---|
| 301 | 2-CN | (oxadiazole) |
| 302 | 2-CN | (oxadiazole) |

TABLE 3-continued

| Formula | R₁ | A |
|---|---|---|
| 303 | 4-CN | (N—N, O ring with CH(CH₃)₂) |
| 304 | 4-CN | (N—N, O ring with CH₂OCH₃) |
| 305 | 4-CONH₂ | (N—N, O ring with C₂H₅) |
| 306 | 4-COOH | (N—N, O ring with C₂H₅) |
| 307 | 2-CN | (triazine ring with N, N, N) |
| 308 | 2-CN | (ring with N, N, OCH₃, OCH₃) |
| 309 | 4-COOCH₃ | (O—N, N ring with CH₃) |
| 310 | 2-CN | (N, N ring with CH₃, CH₃) |
| 311 | 2-CN | (O—N ring) |
| 312 | 2-CN | (N, N ring with C₆H₅) |
| 313 | 2-CN | (N, N ring with OC₂H₅, OC₂H₅) |
| 314 | 4-CN | (N—N, O ring with CH₂–C₆H₅) |
| 315 | 2-CN | (O—N, N ring with CH₂–C₆H₅) |
| 316 | 2-CN | (N—N, O ring with CH₂–C₆H₅) |
| 317 | 2-CN | (N, N ring with SC₂H₅, SC₂H₅) |
| 318 | 2-CN | (N, N ring with NH₂, NH₂) |
| 319 | 2-CN | (N, N ring with OCH₃, NHCH₃) |
| 320 | 2-CN | (N, N ring with N(CH₃)₂, N(CH₃)₂) |
| 321 | 4-CN | (N—N, O ring with OC₂H₅) |
| 322 | 4-CN | (N—O, N ring with OC₂H₅) |

EXAMPLE 4

In a dyeing apparatus, polyester fabric is treated at a liquor ratio 1:20 with an aqueous bath which contains 0.1%, relative to the weight of the fabric, of the compound of the formula (103) and 1 g/liter of the condensation product of 35 mol of ethylene oxide and 1 mol of stearyl alcohol. The bath is then heated within 30 minutes from 40° to 130° C., is held at this temperature for 30 minutes and is then cooled within 15 minutes to 15°

C. The fabric is then rinsed in running deionised water and dried at 70° C. The polyester fabric treated in this way shows a strong brightening effect.

If, in place of the above compound of the formula (103) a compound of the formula (102), (106), (116), (117), (119), (122) or (202) is used in the above instructions, similarly good brightening effects are obtained.

EXAMPLE 5

Polyester fabric is padded at room temperature with an aqueous dispersion which, per liter, contains 0.5 g of the compound of the formula (103) and 1 g of an adduct of about 8 mol of ethylene oxide and 1 mol of p-tert.-octylphenol. The liquor pick-up is 60 to 70%. The fabric is dried at 80° C. and then heated for 30 seconds to 220° C. The fabric treated in this way shows an excellent brightening effect.

If, in place of the above compound of the formula (103), a compound of the formula (102), (106), (112), (116), (117), (119), (120), (121) or (201) is used in the above instructions, similarly good brightening effects are obtained.

EXAMPLE 6

A polyester fabric is padded at room temperature with an aqueous dispersion which, per liter, contains 0.5 g of a brightener mixture, consisting of 2 parts of the compound of the formula (103) and 1 part of the compound of the formula

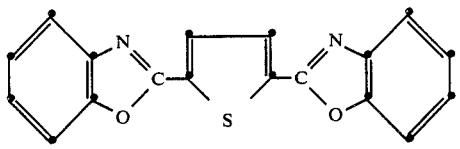

and 1 g of an adduct of about 8 mol of ethylene oxide and 1 mol of p-tert.-octylphenol. The liquor pick-up is 60–70%. The fabric is dried at 100° C. and then heated for 30 seconds to 200° C.

The fabric treated in this way shows an excellent brightening effect of good light fastness.

EXAMPLE 7

A polyester fabric is treated in accordance with the instructions given in Example 6, but the brightener mixture used there is replaced by one of the brightener mixtures A–K listed in Table 4 which follows.

TABLE 4

| Mixture | Component 1 | Component 2 |
|---|---|---|
| A | 3 parts of the compound of the formula (102) | 1 part of the compound of the formula 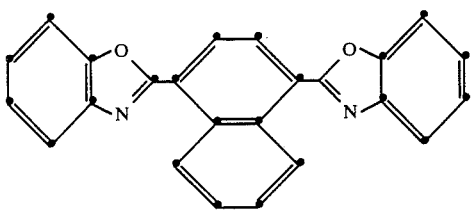 |
| B | 1 part of the compound of the formula (103) | 1 part of the compound of the formula 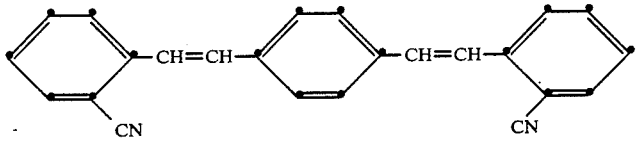 |
| C | 1 part of the compound of the formula (102) | 2 parts of the compound of the formula 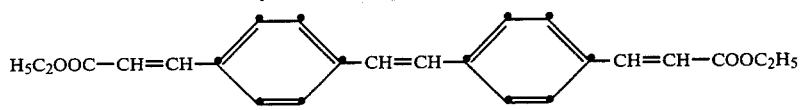 |
| D | 1 part of the compound of the formula (103) | 1 part of the compound of the formula 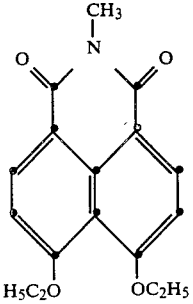 |
| E | 3 parts of the compound | 1 part of the compound of the formula |

TABLE 4-continued

| Mixture | Component 1 | Component 2 |
|---|---|---|
| | of the formula (106) | [benzoxazole-CH=CH-benzoxazole with CH₃ substituents] |
| F | 1 part of the compound of the formula (106) | 1 to 2 parts of the compound of the formula [pyrazole-stilbene structure with H₃C and O substituents] |
| G | 1 part of the compound of the formula (106) | 1 part of the compound of the formula [biphenyl-CH=CH-phenyl-benzoxazole with two CH₃ groups] |
| H | 1 part of the compound of the formula (106) | 1 part of the compound of the formula NC—CH=CH—[phenyl]—CH=CH—[phenyl]—CH=CH—CN |
| I | 1 part of the compound of the formula (102) | 1 part of a mixture of 99% of the compound of the formula NC—[phenyl]—CH=CH—[phenyl]—CH=CH—[phenyl]-CN and 1% of the compound of the formula NC—[phenyl]—CH=CH—[phenyl]—CH=CH—[phenyl]—CN |
| K | 9 parts of the compound of the formula (102) | 1 part of the compound of the formula [pyrene derivative with N=C(OCH₃)—N—N=C(OCH₃) substituents] |

Every polyester fabric treated with the particular brightener mixture shows an excellent brightening effect.

EXAMPLE 8

A woven tricot of polyamide-6,6 is treated in a dyeing apparatus at a liquor ratio of 1:20 with an aqueous bath which contains 0.2%, relative to the weight of the fabric, of a compound of the formula (106), (113), (117) or (118) and 1 g/l of an alkylphenol polyglycol ether. The bath is heated within 30 minutes to 130° C., held for 30 minutes at this temperature and then cooled within 15 minutes to 40° C. The fabric is then rinsed in running deionised water and dried at 180° C. by means of an iron. The polyamide fabric treated in this way shows a strong brightening effect in all 4 cases.

What is claimed is:

1. A 4-heterocyclylvinyl-4'-styryl-biphenyl of the formula

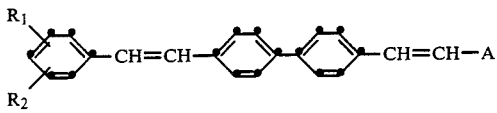

wherein:

A is a radical of the formula

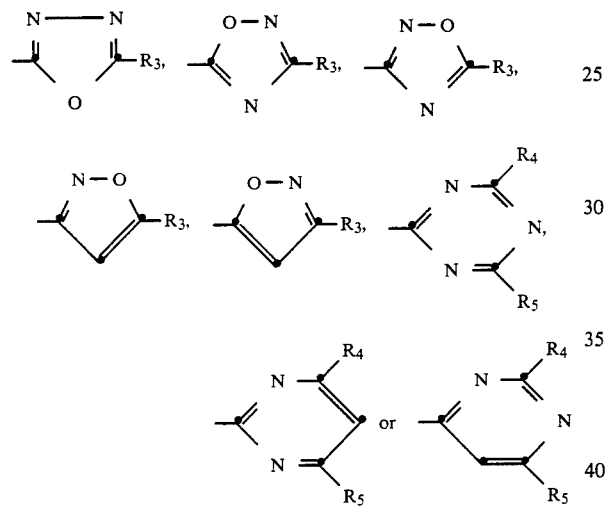

R1 is hydrogen or a non-chromophoric substituent selected from the group consisting of:
(1) alkyl, alkoxy, alkenyl, cycloalkyl, aryl, aralkyl, pyridyl, alkoxycarbonyl, cyano, alkylsulfonyl, alkoxysulfonyl, acyl, acylamino, hydroxyl, alkylmercapto, aryloxy, aralkoxy, alkenyloxy, aryloxycarbonyl, aryloxysulfonyl, aralkoxycarbonyl, carboxyl, sulfo, halogen, acyloxy, trifluoromethyl, amino, alkoxyalkyl, and mono- or dialkylamino;
(2) optionally substituted aminocarbonyl, alkoxycarbonyl and aminosulfonyl; and
(3) alkyl and alkoxy substituted with hydroxyl, alkoxy, alkoxyalkoxy, hydroxyalkoxy, halogen, cyano, aryl, sulfo, carboxyl, carboxy and aminocarbonyl; and R2 is hydrogen, halogen or alkyl;
R3 is hydrogen or a non-chromophoric substituent selected from the group consisting of:
(1) alkyl, alkoxy, alkenyl, cycloalkyl, benzyl, pyridyl, alkoxycarbonyl, cyano, alkylsulfonyl, alkoxysulfonyl, acyl, acylamino, hydroxyl, alkylmercapto, aryloxy, aralkoxy, alkenyloxy, aryloxycarbonyl, aryloxysulfonyl, aralkoxycarbonyl, carboxyl, sulfo, halogen, acyloxy, trifluoromethyl, amino, alkoxyalkyl, and mono- or dialkylamino;
(2) optionally substituted aminocarbonyl, alkoxycarbonyl and aminosulfonyl; and
(3) alkyl and alkoxy substituted with hydroxyl, alkoxy, alkoxyalkoxy, hydroxyalkoxy, halogen, cyano, aryl, sulfo, carboxyl, carboxy and aminocarbonyl; and R4 and R5, independently of one another, are non-chromophoric substituents selected from the group consisting of hydrogen, C1–C4-alkyl, C1–C4-alkoxy, chlorine, C2–C8-alkoxyalkyl, C1–C4-alkylmercapto, amino, C1–C4-alkylamino and C2–C6-dialkylamino.

2. A 4-heterocyclylvinyl-4'-styryl-biphenyl according to claim 1 wherein R1 is hydrogen, C1–C4-alkylsulfonyl, phenylsulfonyl, C1–C4-alkoxysulfonyl, cyano, a sulfo group and salts thereof, a carboxyl group and salts thereof or a group of the formula —COOY(1), —CONY(1)Y(2) or —SO2NY(1)Y(2) in which —Y(1) and Y(2) independently of one another are hydrogen, C1–C4-alkyl or benzyl.

3. A 4-heterocyclylvinyl-4'-styryl-biphenyl according to claim 2 wherein R1 is hydrogen, cyano, C1–C4-alkylsulfonyl or COOY(1) wherein Y(1) is hydrogen or C1–C4-alkyl.

4. A 4-heterocyclylvinyl-4'-styryl-biphenyl according to claim 1 wherein R3 is hydrogen, alkyl, pyridyl, benzyl, alkylalkoxy or alkylmercapto.

5. A 4-heterocyclylvinyl-4'-styryl-biphenyl according to claim 1 wherein:
R1 is C1–C4-alkylsulfonyl, cyano, carboxy or C2–C5-alkoxycarbonyl;
R2 is hydrogen, halogen or alkyl; and
A is a radical of the formula

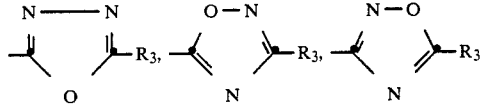

wherein R3 is hydrogen, alkyl, pyridyl, benzyl, alkylalkoxy or alkylmercapto.

6. A 4-heterocyclylvinyl-4'-styryl-biphenyl according to claim 5 wherein R1 is cyano, C1–C4-alkylsulfonyl or C2–C5-alkoxycarbonyl and R2 is hydrogen.

7. A 4-heterocyclylvinyl-4'-styryl-biphenyl according to claim 6 wherein A is

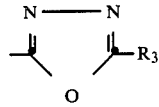

and R1 is cyano and R3 is C1–C4-alkyl.

8. A 4-heterocyclylvinyl-4'-styryl-biphenyl according to claim 7 wherein R1 is 2-cyano and R3 is methyl.

9. An agent for fluorescent brightening of high-molecular organic materials, comprising one or more 4-heterocyclylvinyl-4'-styryl-biphenyls as defined in claim 1, said high-molecular organic materials being selected from polymerization products based on organic compounds containing at least one polymerizable carbon-carbon double bond, polymerization products which are obtained by ring opening, polycondenzation products or precondensate based on bi-functional or poly-functional compounds with condensable groups, poly-addition products, cellulose esters of different degrees of esterification, cellulose ethers, regenerated cellulose, casein plastics, cotton, wool, linen, silk, natural lacquer resins, starch, casein, and after-treatment products thereof.

10. An agent of claim 9, further comprising one or more fluorescent brighteners selected from the group consisting of 1,4-bis-styrylbenzenes, 4-benzoxazolylstilbenes, 4,4'-divinylstilbenes, naphthalimides, 4,4'-bis-styrylphenyls, 4,4'-bis-triazolylstilbenes, bis-benzoxazolyl-thiophenes, -naphthalenes and -ethylenes, oxadiazolyl-stilbenes, naphthotriazol-2-yl-stilbenes, triazinylpyrenes, 2-styryl-benzoxazoles and the coumarins.

11. An agent of claim 10, comprising, as the active brightener substance, 10–99% of said 4-heterocyclylvinyl-4'-styryl-biphenyl and 90–1% of one or more optical brighteners from the classes defined in claim 10.

12. An agent of claim 10, in which the brightener from the classes listed in claim 10 is a polyester brightener.

13. An agent according to claim 12, comprising, as the polyester brightener, 1,4-bis-(benzoxazol-2-yl)-naphthalene, 1-(4'-methoxycarbonylphenyl)-2-(5',6'dimethylbenzoxazol-2'yl)-ethylene, 4,4'-bis-(ethoxycarbonyl-vinyl)-stilbene, 4,4'-bis(cyanovinyl)-stilbene, 1,4-bis-(2'-cyanostyryl)-benzene, 1,5-bis-(benzoxazol-2'-yl)-thiophene, 4-phenyl-4'-(5'',7''-dimethylbenzoxazol-2''-yl)-stilbene, 1,2-bis-(5'-methylbenzoxazol-2'-yl)-ethylene, 4-(benzoxazol-2'-yl)-4'-(3''-methyl-1'',2'',4''-oxadiazol-5''-yl)-stilbene or 2,4-dimethoxytriazin-6-yl-pyrene, the quantity ratio to the 4-heterocyclylvinyl-4'-styryl-biphenyl being 1:2 to 2:1.

14. A process for the fluorescent brightening of a natural, semi-synthetic or synthetic high-molecular weight organic substance selected from cellulose esters of different degrees of esterification, cellulose ethers, regenerated cellulose, their aftertreatment products, casein products, polymerization products based on organic compounds containing at least one polymerizable carbon-carbon double bond, polymerization products obtained by ring opening, poly-condensation products or pre-condensates based on bi-functional or poly-functional compounds with condensable groups, poly-addition products, and after-treatment products thereof, which comprises incorporating into or applying to said natural semi-synthetic or synthetic high-molecular weight organic material a compound as defined in claim 1.

15. A process of claim 14, wherein the organic material is polyester or polyamide.

16. A process of claim 15 wherein 0.001 to 2% of the brightener compound relative to the weight of the organic material, is incorporated in or applied to the organic material.

17. A high-molecular weight organic material selected from the group consisting of polymerization products based on organic compounds containing at least one polymerisable carbon-carbon double bond, polymerization products which are obtainable by ring opening, polycondensation products or pre-condensates based on bi-functional or polyfunctional compounds with condensable groups, polyaddition products, cellulose esters of different degrees of esterification, cellulose ethers, regenerated cellullose, after-treatment products thereof, casein plastics, cotton, wool, linen, cotton silk, natural lacquer resins, starch, and casein which contains 0,001 to 2% of a fluorescent brightener of claim 1.

18. A method of optically brightening a substrate selected from polymerization products based on organic compounds containing at least one polymerizable carbon-carbon double bond, polymerization products which are obtainable by ring opening, polycondensation products or pre-condensates based on bi-functional or poly-functional compounds with condensable groups, poly-addition products, cellulose esters of different degrees of esterification, cellulose ethers, regenerated cellulose, after treatment products thereof, casein plastics, cotton, wool, linen, silk, natural lacquer resins, starch, and casein which comprises incorporating a compound of claim 1 into said substrates or applying said compound to said substrates.

19. The agent of claim 10 wherein said fluorescent brightener is selected from the triazolyl- or pyrazolyl-coumarins.

20. The agent of claim 11 wherein said one or more fluorescent brighteners are present in an amount of 70 to 30%.

21. The process of claim 14 wherein said natural, semi-synthetic, or synthetic high molecular organic materials are textile fibers.

22. The process of claim 15 wherein said material is polyester fibers.

23. The process of claim 16 wherein said brightener or brightener mixture is incorporated into the material or applied to the material to be brightened in an amount of 0.01 to 0.5% relative to the weight of the material.

24. The high molecular organic materials of claim 17 containing 0.01 to 0.5% of the fluorescent brightener or brightener mixture.

25. The material of claim 18 wherein said high-molecular weight organic material is polyester fiber.

26. The method of claim 17 wherein said high-molecular weight organic material is selected from polyester or polyamide.

27. The method of claim 26 wherein said high-molecular weight organic material is polyester fiber.

* * * * *

UNITED STATES PATENT AND TRADEMARK OFFICE
CERTIFICATE OF CORRECTION

PATENT NO. : 4,666,627
DATED : MAY 19, 1987
INVENTOR(S) : HANS RUDOLF MEYER

It is certified that error appears in the above—identified patent and that said Letters Patent is hereby corrected as shown below:

On the cover page, Item [30], Foreign Application Priority Data, should read -- August 5, 1983 [CH] Switzerland.......4266/83-7 --.

Signed and Sealed this

Eighth Day of March, 1988

Attest:

DONALD J. QUIGG

Attesting Officer

Commissioner of Patents and Trademarks